United States Patent
Mueller et al.

(10) Patent No.: US 7,411,081 B2
(45) Date of Patent: Aug. 12, 2008

(54) PROCESS FOR PREPARING AND ORGANOMETALLIC FRAMEWORK MATERIAL

(75) Inventors: Ulrich Mueller, Neustadt (DE); Gerald Lippert, Lambsheim (DE); Olga Schubert, Ludwigshafen (DE); Michael Hesse, Worms (DE); Reinhard Hess, Ellerstadt (DE); Michael Stoesser, Neuhofen (DE); Omar M. Yaghi, Ann Arbor, MI (US)

(73) Assignees: BASF Aktiengesellschaft, Ludwigshafen (DE); The Regents of the University of Michigan, Ann Arbor, MI (US)

( * ) Notice: Subject to any disclaimer, the term of this patent is extended or adjusted under 35 U.S.C. 154(b) by 115 days.

(21) Appl. No.: 10/755,231

(22) Filed: Jan. 13, 2004

(65) Prior Publication Data

US 2005/0154222 A1   Jul. 14, 2005

(51) Int. Cl.
*C07F 3/06* (2006.01)
*C07F 15/00* (2006.01)
*C07F 15/02* (2006.01)
*B01J 31/12* (2006.01)

(52) U.S. Cl. .................. 556/118; 556/46; 556/131; 556/136; 556/138

(58) Field of Classification Search .......... 556/46, 556/118, 131, 136, 138
See application file for complete search history.

(56) References Cited

U.S. PATENT DOCUMENTS

| 6,617,467 | B1 * | 9/2003 | Muller et al. ............ 558/265 |
| 2003/0004364 | A1 | 1/2003 | Yaghi et al. |
| 2005/0154222 | A1 | 7/2005 | Muller et al. |

FOREIGN PATENT DOCUMENTS

WO    WO 03/102000 A1    12/2003

OTHER PUBLICATIONS

U.S. Appl. No. 10/580,407, filed May 24, 2006, Mueller, et al.

\* cited by examiner

*Primary Examiner*—Rosalynd Keys
(74) *Attorney, Agent, or Firm*—Oblon, Spivak, McClelland, Maier & Neustadt, P.C.

(57) ABSTRACT

A process for preparing an organometallic framework material comprising reacting at least one metal salt with at least one at least bidentate compound capable of coordination to the metal ion of said metal salt, in the presence of an aqueous solvent system and at least one base wherein at least one bidentate compound comprises at least carboxy group and at least one further group which is not a carboxy group and which is capable of forming a hydrogen bridge linkage.

25 Claims, 2 Drawing Sheets

PROCESS FOR PREPARING AND ORGANOMETALLIC FRAMEWORK MATERIAL

The present application is directed to a novel process of preparing an organometallic framework material, the organometallic framework obtainable by the novel process and the use of the novel organometallic framework materials. The novel process is comprises reacting at least one metal salt with at least one at least bidentate compound capable of coordinating to the metal ion of said metal salt, in the presence of an aqueous solvent system and at least one base wherein at least one bidentate compound comprises at least two carboxy groups and at least one further group which is not a carboxy group and which is capable of forming a hydrogen bridge linkage.

Organometallic framework materials are comparatively new porous materials having characteristics which allow for their use in many technical fields such as gas storage, catalysis, absorbers and the like. The term "organometallic framework material" as used in the context of the present invention refers to a porous material which contains at least a metal ion and an at least bidentate organic compound wherein said at least bidentate compound is linked, preferably via a coordinate link, to said metal ion. Examples of such materials are described, e.g., in U.S. Pat. No. 5,648,508, EP-A-0 709 253, WO 02/070526, WO 02/008148, M. O'Keeffe et al., *J. Sol. State Chem.*, 152 (2000) p. 3-20, H. Li et al., *Nature* 402 (1999) p. 276 seq., M. Eddaoudi et al., *Topics in Catalysis* 9 (1999) p. 105-111, B. Chen et al., *Science* 291 (2001) p. 1021-23.

Among the starting materials from which the organometallic framework materials are prepared, compounds are preferred which have carboxy groups and simultaneously at one or more other groups which are different from carboxy groups and which are capable of forming, at a given pH of the synthesis mixture, a hydrogen bridge linkage. A specific example for such a group capable of forming a hydrogen bridge linkage is a hydroxy group. For these starting materials, the process for preparing the respective organometallic framework materials known in the art comprise the use of solvents such as dimethylformamide (DMF), diethylformamide (DEF), or N-methylpyrrolidone (NMP) and therefore solvents which are known to be critical for physical health.

Therefore, it is an object of the present invention to provide a process for preparing an organometallic framework material starting from at least bidentate compounds having carboxy groups and at least one other group which is capable of forming a hydrogen bond linkage, which process avoids the use of critical solvents.

It is another object of the present invention to provide a process for preparing an organometallic framework material starting from at least bidentate compounds having carboxy groups and at least one other group which is capable of forming a hydrogen bond linkage, which process makes use of a cheap solvent or solvent system which is comparatively simply to provide.

It is yet another object of the present invention to provide a process for preparing an organometallic framework material starting from at least bidentate compounds having carboxy groups and at least one other group which is capable of forming a hydrogen bond linkage, which process results in an organometallic framework material having a low nitrogen content.

It is still another object of the present invention to provide the organometallic framework material which is obtainable by the novel process and, according to a preferred embodiment of the present invention, has a nitrogen content as low as possible.

Therefore, the present invention is directed to a process for preparing an organometallic framework material comprising reacting at least one metal salt with at least one at least bidentate compound capable of coordinating to the metal ion of said metal salt, in the presence of an aqueous solvent system and at least one base wherein at least one bidentate compound comprises at least two carboxy groups and at least one further group which is not a carboxy group and which is capable of forming a hydrogen bridge linkage.

In principle, a mixture of two or more different at least bidentate compounds may be used as starting materials. In this context, it is possible to use two or more different compounds wherein each compound has at least two carboxy groups and at least one further group which is not a carboxy group and which is capable of forming a hydrogen bridge linkage. It is also possible to use a mixture of two or more different at least bidentate compounds wherein at least one compound has at least two carboxy groups and at least one further group which is not a carboxy group and which is capable of forming a hydrogen bridge linkage, and at least one other compound which either has only one carboxy group and/or has no group which is not a carboxy group and which is capable of forming a hydrogen bridge linkage. Therefore, the at least one other compound may comprise two or more carboxy group an no group which is not a carboxy group and which is capable of forming a hydrogen bridge linkage. It is also possible that the at least one other compound comprises one carboxy group or no carboxy group and either one or more groups which are not a carboxy group and which are capable of forming a hydrogen bridge linkage or no group which is not a carboxy group and which is capable of forming a hydrogen bridge linkage.

Compounds which are different from the compounds having at least two carboxy groups and at least one further group which is not a carboxy group and which is capable of forming a hydrogen bridge linkage, may comprise (i) one carboxy group or (ii) no carboxy group and (i) at least one bidentate functional group or (ii) at least two at least bidentate functional groups from the group $CS_2H$, $NO_2$, $SO_3H$, $Si(OH)_3$, $Ge(OH)_3$, $Sn(OH)_3$, $Si(SH)_4$, $Ge(SH)_4$, $Sn(SH)_3$, $PO_3H$, $AsO_3H$, $AsO_4H$, $P(SH)_3$, $As(SH)_3$, $CH(RSH)_2$, $C(RSH)_3$, $CH(RNH_2)_2$, $C(RNH_2)_3$, $CH(ROH)_2$, $C(ROH)_3$, $CH(RCN)_2$, $C(RCN)_3$, wherein R is an alkyl group having 1, 2, 3, 4, or 5 carbon atoms, or an aryl group consisting of 1 or 2 phenyl rings, $CH(SH)_2$, $C(SH)_3$, $CH(NH_2)_2$, $C(NH_2)_2$, $CH(OH)_2$, $C(OH)_3$, $CH(CN)_2$, and $C(CN)_3$.

All at least bidentate compounds used in the process according to the present invention preferably comprise a linear, branched and/or cyclic alkyl substructure, having 1, 2, 3, 4, 5, 6, 7, 8, 9, or 10 carbon atoms, or an aryl substructure, having 1, 2, 3, 4, or 5 aryl rings such as phenyl groups wherein at least two rings may be condensed as it is the case for, e.g., naphthalene, or an alkyl amine substructure, comprising linear, branched and/or cyclic alkyl groups having 1, 2, 3, 4, 5, 6, 7, 8, 9, or 10 carbon atoms, or an aryl amine substructure having from 1, 2, 3, 4, or 5 aryl rings such as phenyl groups wherein at least two rings may be condensed as it is the case for, e.g., naphthalene. Also compounds comprising at least one alkyl substructure and at least one aryl substructure, or at least one alkyl group and at least one alkyl amine substructure, or at least one alkyl substructure and at least one aryl amine substructure, or at least one aryl substructure and at least one alkyl amine substructure, or at least one aryl substructure and at least one alkyl amine substructure and at least one aryl amine substructure, or at least one alkyl substructure and at least one aryl substructure and at least one alkyl amine substructure, or at least one alkyl substructure and at least one aryl substructure at least one aryl amine substructure, or at least one aryl substructure and at least one alkyl amine substructure and at least one aryl amine substructure, or at least one alkyl substructure and at least one aryl substructure and at least one alkyl amine substructure and at least one aryl amine substructure, are possible.

Especially preferred are substructures having one or more substituted or unsubstituted aromatic nuclei, such as one, two, three or more substituted or unsubstituted aromatic nuclei like, e.g., a benzene substructure or a naphthalene substructure. According to an even more preferred embodiment of the present invention, the at least one bidentate compound is a compound having one aromatic nucleus. Within these preferred embodiments, each aromatic nucleus may independently comprise at least one hetero atom such as S, N, or O. Therefore, also substructures such as pyridine or chinoline are preferred.

According to a preferred embodiment of the present invention, all at least bidentate compounds used in the process for preparing the organometallic framework material have at least two carboxy groups and at least one group which is not a carboxy group and which is capable of forming a hydrogen bond linkage.

The term "carboxy group" as used in the context of the present invention refers to the group —COOH and to the carbonation —COO$^-$.

At least bidentate compounds having two, three, or four carboxy groups are preferred. At least bidentate compounds having three carboxy groups are especially preferred.

Among others, the following compounds having three carboxy groups are preferred wherein the compounds listed below may or may not comprise the at least one group which is not a carboxy group and which is capable of forming a hydrogen bond linkage. In case a compound does not comprise a group which is not a carboxy group and which is capable of forming a hydrogen bond linkage, this compound has to be regarded as a basis structure which, in order to be used according to the invention, has to be suitably substituted with at least one group which is not a carboxy group and which is capable of forming a hydrogen bond linkage:

2-hydroxy-1,2,3-propane tricarboxylic acid, 7-chloro-2,3, 8-quinoline tricarboxylic acid, 1,2,4-benzene tricarboxylic acid, 1,2,4-butane tricarboxylic acid, 2-phosphono-1,2,4-butane tricarboxylic acid, 1,3,5-benzene tricarboxylic acid, 4,5-dihydro-4,5-dioxo-1H-pyrrolo[2,3-F]quinoline-2,7,9-tricarboxylic acid, 5-acetyl-3-amino-6-methylbenzene-1,2,4-tricarboxylic acid, 3-amino-5-benzoyl-6-methylbenzene-1,2,4-tricarboxylic acid, 1,2,3-propane tricarboxylic acid or aurine tricarboxylic acid, Most preferred are at least bidentate compounds having two carboxy groups.

Therefore, the present invention also relates to a process as described above wherein the at least one at least bidentate compound comprises two carboxy groups.

Among others, the following compounds having two carboxy groups are preferred wherein the compounds listed below may or may not comprise the at least one group which is not a carboxy group and which is capable of forming a hydrogen bond linkage. In case a compound does not comprise a group which is not a carboxy group and which is capable of forming a hydrogen bond linkage, this compound has to be regarded as a basis structure which, in order to be used according to the invention, has to be suitably substituted with at least one group which is not a carboxy group and which is capable of forming a hydrogen bond linkage:

1,4-butane dicarboxylic acid, 4-oxopyran-2,6-dicarboxylic acid, 1,6-hexane dicarboxylic acid, decane dicarboxylic acid, 1,8-heptadecane dicarboxylic acid, 1,9-heptadecane dicarboxylic acid, heptadecane dicarboxylic acid, acetylene dicarboxylic acid, 1,2-benzene dicarboxylic acid, 2,3-pyridine dicarboxylic acid, 1,3-butadiene-1,4-dicarboxylic acid, 1,4-benzene dicarboxylic acid, imidazole-2,4-dicarboxylic acid, 2-methylquinoline-3,4-dicarboxylic acid, quinoline-2,4-dicarboxylic acid, quinoxaline-2,3-dicarboxylic acid, 6-chloroquinoxaline-2,3-dicarboxylic acid, 4,4'-diaminophenylmethane-3,3'-dicarboxylic acid, quinoline-3,4-dicarboxylic acid, 7-chloro-4-hydroxyquinoline-2,8-dicarboxylic acid, diimide dicarboxylic acid, pyridine-2,6-dicarboxylic acid, 2-methylimidazole-4,5-dicarboxylic acid, thiophene-3,4-dicarboxylic acid, 2-isopropylimidazole-4,5-dicarboxylic acid, tetrahydropyrane-4,4-dicarboxylic acid, perylene-3,9-dicarboxylic acid, perylene dicarboxylic acid, Pluriol E 200-dicarboxylic acid, 3,6-dioxaoctane dicarboxylic acid, 3,5-cyclohexadiene-1,2-dicarboxylic acid, octane dicarboxylic acid, pentane-3,3-dicarboxylic acid, 4,4'-diamino-1,1'-diphenyl-3,3'-dicarboxylic acid, benzidine-3,3'-dicarboxylic acid, 1,4-bis-(phenylamino)-benzene-2,5-dicarboxylic acid, 1,1'-dinaphthyl-8,8'-dicarboxylic acid, 7-chloro-8-methylquinoline-2,3-dicarboxylic acid, 1-anilinoanthraquinone-2,4'-dicarboxylic acid, polytetrahydrofurane-250-dicarboxylic acid, 1,4-bis-(carboxymethyl)-piperazine-2,3-dicarboxylic acid, 7-chloroquinoline-3,8-dicarboxylic acid, 1-(4-carboxy)-phenyl-3-(4-chloro)-phenyl-pyrazoline-4,5-dicarboxylic acid, 1,4,5,6,7,7,-hexachloro-5-norbornen-2,3-dicarboxylic acid, phenylindane dicarboxylic acid, 1,3-dibenzyl-2-oxoimidazolidine-4,5-dicarboxylic acid, 1,4-cyclohexane dicarboxylic acid, naphthaline-1,8-dicarboxylic acid, 2-benzoylbenzene-1,3-dicarboxylic acid, 1,3-dibenzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecane dicarboxylic acid, O-hydro-xybenzophenone dicarboxylic acid, Pluriol E 300 dicarboxylic acid, Pluriol E 400 dicarboxylic acid, Pluriol E 600 dicarboxylic acid, pyrazole-3,4-dicarboxylic acid, 2,3-pyrazine dicarboxylic acid, 5,6-dimethyl-2,3-pyrazine dicarboxylic acid, 4,4'-diaminodiphenylether-diimide dicarboxylic acid, 4,4'-diaminodiphenylmethane-diimide dicarboxylic acid, 4,4'-diaminodiphenylsulfonediimide dicarboxylic acid, 2,6-naphthalene dicarboxylic acid, 1,3-adamantane dicarboxylic acid, 1,8-naphthalene dicarboxylic acid, 2,3-naphthalene dicarboxylic acid, 8-methoxy-2,3-naphthalene dicarboxylic acid, 8-nitro-2,3-naphthalene dicarboxylic acid, 8-sulpho-2,3-naphthalene dicarboxylic acid, anthracene-2,3-dicarboxylic acid, 2',3'-diphenyl-p-terphenyi-4,4'-dicarboxylic acid, diphenylether-4,4'-dicarboxylic acid, imidazole-4,5-dicarboxylic acid, 4(1H)-oxothiochromene-2,8-dicarboxylic acid, 5-tert-butyl-1,3-benzene dicarboxylic acid, 7,8-quinoline dicarboxylic acid, 4,5-imidazole dicarboxylic acid, 4-cyclohexene-1,2-dicarboxylic acid, hexatriacontane dicarboxylic acid, tetradecane dicarboxylic acid, 1,7-heptane dicarboxylic acid, 5-hydroxy-1,3-benzene dicarboxylic acid, pyrazine-2,3-dicarboxylic acid, furane-2,5-dicarboxylic acid, 1-nonene-6,9-dicarboxylic acid, eicosene dicarboxylic acid, 4,4'-dihydroxydiphenylmethane-3,3'-dicarboxylic acid, 1-amino-4-methyl-9,10-dioxo-9,10-dihydroanthracene-2,3-dicarboxylic acid, 2,5-pyridine dicarboxylic acid, cyclohexene-2,3-dicarboxylic acid,2,9-dichlorofluorubine-4,11-dicarboxylic acid, 7-chloro-3-methylquinoline-6,8-dicarboxylic acid, 2,4-dichlorobenzophenone-2',5'-dicarboxylic acid, 1,3-benzene dicarboxylic acid, 2,6-pyridine dicarboxylic acid, 1-methylpyrrole-3,4-dicarboxylic acid, 1-benzyl-1H-pyrrole-3,4-dicarboxylic acid, anthraquinone-1,5-dicarboxylic acid, 3,5-pyrazole dicarboxylic acid, 2-nitrobenzene-1,4-dicarboxylic acid, heptane-1,7-dicarboxylic acid, cyclobutane-1,1-dicarboxylic acid 1,14-tetradecane dicarboxylic acid, 5,6-dehydronorbornane-2,3-dicarboxylic acid or 5-ethyl-2,3-pyridine dicarboxylic acid.

In principle, there is no restriction with regard to the at least one functional group other than a carboxy group and capable of forming a hydrogen bond linkage. Among others, at least one of the following functional groups other than a carboxy group and capable of forming a hydrogen bond linkage may be comprised in the at least bidentate compound:

an acetal group, a hemiacetal group, an acid azide group, an acid halide group, a hydroxy group, a thiol group, a hydroxamic acid group, an imidic acid group, a nitrolic acid group, a nitrosolic acid group, a peracid group, a sulfenic acid group, a sulfinic acid group, a sulfonic acid group, a thioacid group, an amide group such as a primary or secondary or tertiary amide group, an amidine group, an amidoxime group, an amino group, a cyanate group, an isocyanate group, an isothiocyanate group, a cyanide group, an isocyanide group, a carbylamine group, a betaine group, a disulfide group, an ester group, a hydrate of an aldehyde or a hydrate of a ketone, an acid hydrazide group, a hydrazine group, a hydroperoxide group, a hydroxylamine group, an imide group, a imine group, a lactam group, a lactone group, a nitrile group, a nitrolic acid group, a nitrosolic acid group, an oxime group, a peracid group, a peralcohol group, a sulfide group, a sulfoxide group, an aldehyde group, a thioaldehyde group, a urea group, a thione group, a thioether group or a thioketone group.

According to a preferred embodiment of the present invention, the at least bidentate compound comprises at least one carboxy group and at least one further functional group capable of forming a hydrogen bond linkage, preferably at least one further functional group selected from the group mentioned above, more preferably at least one hydroxy group.

Therefore, the present invention also relates to a process as described above wherein the at least one at least bidentate compound comprises at least one hydroxy group.

According to an even more preferred embodiment of the present invention, at least one of the at least one further functional groups is a hydroxy group. Even more preferably, the at least bidentate compound has two functional groups being capable of forming a hydrogen bond linkage, and most preferably, both functional groups are hydroxy groups.

Therefore, the present invention also relates to a process as described above wherein the at least one at least bidentate compound comprises two hydroxy groups.

As mentioned above, it is possible to use at least bidentate compounds having at least two carboxy group, most preferably two carboxy groups, and at least one functional group capable of forming a hydrogen bond linkage, preferably at least one hydroxy group, more preferably at least two hydroxy groups and most preferably two hydroxy groups, said groups being linked to one of the above-mentioned substructure such as an alkyl substructure, an aryl substructure, an alkyl amine substructure, an aryl amine substructure or one of the mixed structures comprising at least two of said substructures as listed above. According to a preferred embodiment of the present invention, the at least bidentate compounds having at least two carboxy group, most preferably two carboxy groups, and at least one functional group capable of forming a hydrogen bond linkage, preferably at least one hydroxy group, more preferably at least two hydroxy groups and most preferably two hydroxy groups, contain substructures having one or more substituted or unsubstituted aromatic nuclei, such as one, two, three or more substituted or unsubstituted aromatic nuclei like, e.g., a benzene substructure or a naphthalene substructure. Preferably, they contain one aromatic nucleus.

Therefore, at least bidentate compounds having one aromatic nucleus and at least two carboxy groups, preferably two carboxy groups, and at least one hydroxy group, more preferably at least two hydroxy groups and most preferably two hydroxy groups are preferred. As aromatic nucleus, the benzene nucleus is preferred.

Therefore, the present invention also relates to a process as described above wherein the at least one bidentate compound is dihydroxy terephthalic acid.

The term "aqueous solvent system" as used in the context of the present invention refers to a solvent system in which water is used as the only solvent and to a system containing water as solvent and at least one further solvent wherein the system contains at least 10 wt.-% of water, based on the total weight of all solvents used. In case at least one other solvent is used in addition to water, the solvent system preferably contains at least 20 wt.-%, more preferably at least 30 wt.-%, even more preferably at least 40 wt.-%, still more preferably at least 50 wt.-%, still more preferably at least 60 wt.-%, still more preferably at least 70 wt.-%, still more preferably at least 80 wt.-%, still more preferably at least 90 wt.-%, still more preferably at least 95 wt.-% of water, based on the total weight of all solvents used.

In principle, each solvent may be used in addition to water. According to a preferred embodiment of the present invention, the at least one solvent which is used in addition to water comprises at least one hydroxy group such as one hydroxy group, two hydroxy groups, three hydroxy groups or more hydroxy groups. Examples for these solvents are alcohols such as primary, secondary or tertiary alcohols, glycols, triols, polyols, polyether-alcohols and the like.

According to another embodiment of the present invention, in case the reaction is at least partially carried out in supercritical phase, the aqueous solvent system may comprise supercritical carbon dioxide.

Therefore, the present invention also relates to a process as described above wherein the aqueous solvent system comprises water and at least one compound comprising at least one hydroxy group.

According to a preferred embodiment of the present invention, the at least one compound comprising at least one hydroxy group which is used in addition to water in the solvent system is an alcohol having 1, 2, 3, 4, 5, or 6 C atoms, more preferably 1, 2, 3, 4, or 5 C atoms, even more preferably 1, 2, 3, or 4 C atoms. Therefore, alcohols such as methanol, ethanol, n-propanol, isopropanol, n-butanol, isobutanol or tert-butanol are preferred. Especially preferred are methanol, ethanol, n-propanol, and isopropanol.

Therefore, the present invention also relates to a process as described above wherein wherein the aqueous solvent system comprises at least-one alcohol selected from the group consisting of methanol, ethanol, n-propanol, and isopropanol.

According to an especially preferred embodiment of the present invention, the at least one solvent which is optionally used in addition to water does not contain nitrogen.

As far as the at least one base is concerned which is used in the process according to the invention, each base may be used which is at least partially soluble or miscible in the aqueous solvent system.

As bases, nitrogenous bases such as dimethyl formamide (DMF), diethyl formamide (DEF), n-methylpyrrolidone (NMP), triethyl amine, pyridine; phosphorous bases; hydroxy bases such as alkali hydroxides such as lithium hydroxide, sodium hydroxide, potassium hydroxide, alkaline earth hydroxides such as, e.g., magnesium hydroxide, calcium hydroxide, or strontium hydroxide, or basic metal hydroxides such as $Zn_4O(OH)_6$ or zinc hydroxy carbonate $[ZnCO_3]_2[Zn(OH)_2]_3$ or magnesium hydroxy carbonate may be mentioned. Especially preferred are bases which do not contain nitrogen.

Therefore, the present invention relates to a process as described above wherein the at least one base is an alkali metal hydroxide, an alkaline earth metal hydroxide and/or a basic metal hydroxide which is at least partially soluble or miscible in the aqueous solvent system.

According to a preferred embodiment of the present invention, the at least one base is an alkali hydroxide and/or an alkaline earth hydroxide. Especially preferred is an alkali hydroxide such as lithium hydroxide, sodium hydroxide, potassium hydroxide, or rubidium hydroxide, more preferred is sodium hydroxide and/or potassium hydroxide.

Therefore, the present invention also relates to a process as described above wherein the at least one base is sodium hydroxide or potassium hydroxide or a mixture of sodium hydroxide and potassium hydroxide.

The pH of the reaction mixture in which the organometallic framework material is synthesized is preferably in the range of from 3 to 9.

Therefore, the present invention also relates to a process as described above wherein the reaction of the at least one metal salt with the at least one bidentate compound is carried out at a pH in the range of from 3 to 9.

More preferably, the pH of the reaction mixture is in the range of from 5 to 8.5, even more preferably in the range of from 7.0 to 8.0, still more preferably in the range of from 7.0 to 7.9, still more preferably in the range of from 7.1 to 7.8, still more preferably in the range of from 7.2 to 7.7 and especially preferably in the range of from 7.3 to 7.6.

Therefore, the present invention also relates to a process as described above wherein the reaction of the at least one metal salt with the at least one bidentate compound is carried out at a pH in the range of from 7.3 to 7.6.

The pH values given in the context of the present invention refer to values determined by measurmenet with a pH meter (membrane glass electrode).

Depending of the at least one at least bidentate compound, the at least one base and the aqueous solvent system, it may be necessary to adjust the pH of the reaction mixture to a certain value or to a certain range mentioned above. Thus, according to a preferred embodiment of the present invention, the pH of the reaction mixture is adjusted by adding at least one suitable acid and/or at least one suitable base.

As suitable acids, all acids may be mentioned which do not influence the structure of the organometallic framework or the process of building up the structure of the organometallic framework. Preferred acids are inorganic acids such as mineral acids like HCl, $HNO_3$, $H_2SO_4$, $H_3PO_4$, monocarboxylic acids such as formic acid, acetic acid, propionic acid, and dicarboxylic acids such as oxalic acid and malic acid.

According to a preferred embodiment of the present invention, at least one acid is used to adjust the pH of the reaction mixture which can be removed from the organometallic framework material in which the acid may be incorporated after the synthesis and/or removed from the, reaction system by applying increased temperature such as by at least one drying step and/or by at least one calcination step. Among these acids, formic acid and/or nitric acid are especially preferred.

According to another preferred embodiment of the present invention, inorganic acids like, e.g HCl, $H_2SO_4$, $H_3PO_4$, are used to adjust the pH value of the reaction mixture Hydrochloric acid is especially preferred.

As to the metal component within the framework material that is to be used according to the present invention, particularly to be mentioned are the metal ions of the main group elements and of the subgroup elements of the periodic system of the elements, namely of the groups Ia, IIa, IIIa, IVa to VIIIa and Ib to VIb. Among those metal components, particular reference is made to Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Al, Ga, In, Tl, Si, Ge, Sn, Pb, As, Sb, and Bi, more preferably to Zn, Cu, Ni, Pd, Pt, Ru, Rh and Co. As to the metal ions of these elements, particular reference is made to: $Mg^{2+}$, $Ca^{2+}$, $Sr^{2+}$, $Ba^{2+}$, $Sc^{3+}$, $Y^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^{+}$, $Ir^{2+}$, $Ir^{+}$, $Ni^{2+}$, $Ni^{+}$, $Pd^{2+}$, $Pd^{+}$, $Pt^{2+}$, $Pt^{+}$, $Cu^{2+}$, $Cu^{+}$, $Ag^{+}$, $Au^{+}$, $Zn^{2+}$, $Cd^{2+}$, $Hg^{2+}$, $Al^{3+}$, $Ga^{3+}$, $In^{3+}$, $Tl^{3+}$, $Si^{4+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^{+}$, $Sb^{5+}$, $Sb^{3+}$, $Sb^{+}$, $Bi^{5+}$, $Bi^{3+}$ and $Bi^{+}$.

In general, the at least one metal ion may be introduced in every conceivable method provided that, in the reaction mixture, the metal is present as the respective ion. Therefore, every conceivable metal ion precursor may be used. According to a preferred embodiment, the at least one metal ion is introduced in the reaction mixture as salt, even more preferably as at least one solution of the salt in at least one suitable solvent.

As solvent for the at least one metal salt, most preferably at least one solvent of the aqueous solvent system as described above is used. Therefore, according to one embodiment of the present invention, at least one solvent of the aqueous solvent system is at least partially introduced in the reaction mixture via the solution of the at least one metal salt.

Particularly preferred metal salts are salts of Zn, Cu, Co, Ni, Pd, Pt, Ru, Rh, Fe and mixtures of two or more thereof.

Therefore, the present invention also relates to a process as described above wherein the at least one metal salt is a salt of Zn, Cu, Co, Ni, Pd, Pt, Ru, Rh, Fe and mixtures of two or more thereof.

According to an even more preferred embodiment, the present invention relates to a process as described above wherein the metal salt is a salt of Zn, Co, Cu and/or Fe.

As far as the counterions of the metal ions are concerned, no specific limitations exist. Among others, inorganic ions such as sulfate, nitrate, nitrite, sulfite, bisulfite, phosphate, hydrogen phosphate, dihydrogen phosphate, diphosphate, triphosphate, phosphite, chloride, chlorate, bromide, bromate, iodide, iodate, carbonate, and bicarbonate are preferred. As to organic counterions which may be used as well, acetates, formates and oxalates are preferred.

Especially preferred are inorganic anions, with nitrate being especially preferred.

According to one aspect of the present invention where the organometallic framework material must not be treated under calcination conditions due to, e.g., temperature sensitivity, it is preferred not to use nitrate containing acids or salts but acids or salts which allow for being washed out of the framework.

In addition to the metal salts, other metallic compounds may be used, such as sulfates, phosphates and other complex counter-ion metal salts of the main- and subgroup metals of the periodic system of the elements. Metal oxides, mixed oxides and mixtures of metal oxides and/or mixed oxides with or without a defined stoichiometry are preferred. All of the above mentioned metal compounds can be soluble or insoluble and they may be used as starting material either in form of a powder or as a shaped body or as any combination thereof.

According to an especially preferred embodiment of the present invention, the reaction is carried out in absence of a templating agent.

The reaction may be carried out in one or more batch reactors or as a continuous process in at least one continuous reactor such as a tube reactor, a tube bundle reactor, a continuous stirred tank reactor (CSTR) or a cascade of CSTRs. According to an especially preferred embodiment of the present invention, the novel process is carried out in a batch reactor.

The pressure under which the reaction according to the invention is carried out and the temperature at which the reaction according to the invention is carried out are generally chosen so that the reaction mixture in which the organometallic framework material is prepared is at least partially liquid.

The reaction is preferably carried out at a temperature in the range of above the freezing point of the aqueous solvent system and below the boiling point of the aqueous solvent system at a given pressure. More preferably, the reaction is carried out at a temperature in the range of from 0 to 130° C., even more preferably in the range of from 5 to 100° C., still more preferably in the range of from 10 to 90° C., more preferably in the range of from 15 to 70° C. and especially preferably in the range of from 20 to 50° C. According to a further especially preferred embodiment, the reaction is carried out at about room temperature.

The pressure under which the reaction is carried out may be adapted to the temperatures mentioned above so that, according to a preferred embodiment of the present invention, the reaction mixture is at least partially liquid. According to an especially preferred embodiment, the reaction is carried out at about the pressure which establishes during of the reaction. According to another preferred embodiment, the reaction is carried out at normal pressure.

The sequence of mixing the starting materials is generally not critical.

According to a preferred embodiment of the present invention, the at least one bidentate compound is first at least partially dissolved in at least a part of the aqueous solvent system which contains at least one suitable base.

In an optional second step, if necessary, the pH of the resulting mixture is adjusted to a value within one of the above-mentioned preferred ranges, preferably in the range of from 5 to 8.5, even more preferably in the range of from 7.0 to 8.0, still more preferably in the range of from 7.0 to 7.9, still more preferably in the range of from 7.1 to 7.8, still more preferably in the range of from 7.2 to 7.7 and especially preferably in the range of from 7.3 to 7.6, by either adding at least one suitable acid or at least one suitable base, preferably by adding at least one suitable acid as described above in detail. If necessary, the at least one acid or the at least base may be dissolved in at least one suitable solvent prior to the addition to the reaction mixture. As solvent, at least one compound which is part of the aqueous solvent system is especially preferred.

In a further step, preferably at least one metal salt is added to the mixture. During the addition of the at least one metal salt, the reaction mixture is preferably continuously stirred. According to a preferred embodiment, the at least one metal salt is introduced into the mixture as a solution of the at least one metal salt in at least one suitable solvent. The at least one suitable solvent is more preferably at least one compound of the aqueous solvent system the reaction is carried out in.

In a further step, the at least one suitable base mentioned above is introduced into the resulting mixture comprising the at least one bidentate compound, the aqueous solvent system, the at least one metal salt and optionally the at least one acid. The at least one suitable base is added in an amount so that the pH of the reaction mixture is adjusted to a value within one of the above-mentioned preferred ranges, preferably in the range of from 5 to 8.5, even more preferably in the range of from 7.0 to 8.0, still more preferably in the range of from 7.0 to 7.9, still more preferably in the range of from 7.1 to 7.8, still more preferably in the range of from 7.2 to 7.7 and especially preferably in the range of from 7.3 to 7.6. If necessary, the at least one base may be dissolved in at least one suitable solvent prior to the addition to the reaction mixture. As solvent, at least one compound which is part of the aqueous solvent system is especially preferred.

The reaction according to the invention is carried out, in case the reaction is a batch-type reaction, for a time which is generally in the range of up to 30 h, preferably from 1 to 20 h, more preferably in the range of from 2 to 10 h and especially preferably in the range of from 3 to 5 h.

Once the reaction is at least partially, preferably completely finished, the organometallic framework material is present in its mother liquor, optionally comprising at least one template compound which may be at least partially incorporated in the pores of the organometallic framework material.

The term "mother liquor" as used in the context of the present invention refers to the at least partially liquid phase which results directly from the synthesis step and which contains the organometallic framework material in dissolved and/or suspended form and optionally may contain unreacted components of the synthesis mixture such as the at least one at least bidentate compound.

The separation of the organometallic framework materials from its mother liquor may be achieved by procedures known in the art such as solid-liquid separations, centrifugation, extraction, filtration which, depending on the size of the crystals of the organometallic framework material, may be chosen from at least one filtration method, or such as cake filtration, microfiltration, diafiltration, ultrafiltration, membrane filtration, cross-flow filtration, by flocculation using flocculation adjuvants such as non-ionic, cationic and/or anionic adjuvants, or by the addition of pH shifting additives such as salts, acids or bases, by flotation, by spray drying, by spray granulation, as well as by evaporation of the mother liquor at elevated temperature and/or in vacuo and concentrating of the solid. A preferred method of separating the organometallic framework material from its mother liquor is chosen from the group consisting of slid-liquid-separation, centrifugation, extraction, spray drying, filtration such as membrane filtration, cross-flow filtration, cake filtration, diafiltration, ultrafiltration, flocculation by using flocculation adjuvants such as non-inonic, cationic or anionic adjuvants, pH shift by adding suitable additives such as salts, acids or bases, flotation, spray granulation or evaporation of the mother liquor at elevated temperature or in vacuo and concentration of the solid material.

According to a preferred embodiment of the present invention, the organometallic framework material obtained after the separation is typically a fine powder having a crystal size of from 0.1 to 100 μm, determined via SEM (scanning electron microscopy).

After the separation of the organometallic framework material from its mother liquor, the powder material may be washed at least once and/or dried at least once and/or calcined at least once.

According to a preferred embodiment of the present invention, the organometallic framework material separated from its mother liquor is first washed at least once and then dried. As washing agent, at least one compound of the aqueous solvent system is used. More preferably, the organometallic framework material separated from its mother liquor is washed with water.

The preferably washed organometallic framework material is then dried wherein the applied temperature is preferably chosen so that the at least one washing agent is at least partially, preferably essentially completely removed and the organometallic framework material structure is not destroyed. Drying is carried out, preferably at normal pressure, at a temperature which is generally in the range of from 20 to 120° C., preferably in the range of from 40 to 100° C. and especially preferably in the range of from 50 to 60° C.

Drying may be carried out in vacuo wherein the temperature applied may be adapted so that the at least one washing agent is at least partially, preferably essentially completely removed and the organometallic framework material structure is not destroyed. The drying time is generally in the range of from 0.1 to 15 h, preferably in the range of from 0.2 to 5 h and especially preferably in the range of from 0.5 to 1 h.

Therefore, the present invention also relates to an organometallic framework material comprising at least one metal ion and at least one at least bidentate organic compound coordinately bound to said at least one metal ion, obtainable by a process comprising reacting at least one metal salt with at least one at least bidentate compound capable of coordination to the metal ion of said metal salt, in the presence of an aqueous solvent system and at least one base wherein at least one bidentate compound comprises at least carboxy group and at least one further group which is not a carboxy group and which is capable of forming a hydrogen bridge linkage.

As mentioned above, one advantage of the process according to the present invention is the fact that use is made of a solvent system which does not contain critical compounds and, additionally, does not contain nitrogen containing compounds.

Therefore, the present invention also relates to the organometallic framework material as described above wherein the at least one base is not a nitrogen base and wherein the aqueous solvent system does not comprise a solvent which contains nitrogen.

After washing and drying of the organometallic framework material, the nitrogen content of the material is generally smaller or equal 1 wt.-%, preferably smaller or equal 0.5 wt.-% and especially preferably smaller or equal 0.1 wt.-%, based on the total weight of the material and determined via elemental analysis.

Therefore, the present invention also relates to the organometallic framework material as described above wherein the nitrogen content of the organometallic framework material is smaller or equal 1 wt.-% based on the total weight of the framework material.

The organometallic framework material obtainable by the process according to the present invention comprises pores and particularly micro- and/or mesopores. Micropores are defined as being pores having a diameter of 2 nm or below and mesopores as being pores having a diameter in the range of above 2 nm to 50 nm, respectively, according to the definition given in Pure Applied Chem. 45, p. 71 seq., particularly on p. 79 (1976). The presence of the micro- and/or mesopores can be monitored by sorption measurements for determining the capacity of the organometallic framework material to take up nitrogen at 77 K according to DIN 66131 and/or DIN 66134.

The specific surface area of the organometallic framework material obtainable by the process according to the present invention, determined and calculated according to the Langmuir model (DIN 66131, 66134), is generally greater or equal 5 $m^2/g$, more preferably greater or equal 10 $m^2/g$, and still more preferably greater or equal 20 $m^2/g$. According to even more preferred embodiments of the present invention, the specific surface area is greater or equal 50 $m^2/g$, particularly preferably greater or equal 500 $m^2/g$ and may increase into the region of above 4,000 $m^2/g$.

Therefore, the present invention also relates to the organometallic framework material as described above wherein the specific surface area of said material, determined by nitrogen absorption at 77 K according to DIN 66131 and/or DIN 66134, is greater or equal 20 $m^2/g$.

According to a preferred embodiment of the present invention, the metal ion the at least one at least bidentate compound is linked to is at least one of $Ni^{2+}$, $Ni^+$, $Fe^{3+}$, $Fe^{2+}$, $Ru^{3+}$, $Ru^{2+}$, $Co^{3+}$, $Co^{2+}$, $Rh^{2+}$, $Rh^+$, $Pd^{2+}$, $Pd^+$, $Pt^{2+}$, $Pt^+$, $Cu^{2+}$, $Cu^+$, $Zn^{3+}$. According to an even more preferred embodiment, the metal ion the at least one at least bidentate compound is linked to is at least one of $Zn^{2+}$, $Co^{3+}$, $Co^{2+}$, $Cu^{2+}$, $Cu^+$ and/or $Fe^{3+}$, $Fe^{2+}$. According to an especially preferred embodiment, the metal ion the at least one at least bidentate compound is $Zn^{2+}$, Therefore, the present invention also relates to the organometallic framework material as described above wherein the at least one metal salt is a zinc salt.

The organometallic framework material obtainable by the process of the present invention contains the especially preferred zinc in an amount which is generally in the range of from 25 to 40 wt.-%, preferably in the range of from 30 to 38 wt.-% and especially referred in the range of from 33 to 37 wt.-%, based on the total weight of the dried organometallic framework material.

Therefore, the present invention also relates to the organometallic framework material as described above comprising zinc in the range of from 25 to 40 percent by weight.

The organometallic framework material separated from its mother liquor may be employed as such and in washed and/or dried and/or calcined form. Moreover, it is possible to prepare a shaped body from the organometallic framework material and employ the shaped body containing the organometallic framework material.

In order to produce a shaped body, the separated organometallic framework material may be mixed with inert adjuvants like, e.g., graphite, compounded, melted, extruded, coextruded, pressed, spinned, foamed and/or granulated to form a shaped body or shaped bodies. Possible geometries of the shaped body or shaped bodies are, among others, pellets, pills, spheres, granulate, or extrudates such as strands.

Especially preferred are geometries of the shaped bodies which are especially suitable for the preferred use as described hereinunder.

In the context of the present invention, the term "shaped body" refers to any solid body that has at least a two-dimensional outer contour and extends to at least 0.02 mm in at least one direction in space. No other restrictions apply, i.e., the body may take any conceivable shape and may extend in any direction by any length so long as it extends to at least 0.02 mm in one direction. In a preferred embodiment, the shaped bodies extend from 0.02 to 50 mm in all directions. In a further preferred embodiment, the shaped bodies extend from 1.5 to 5 mm in all directions.

As far as the geometry of these shaped bodies is concerned, spherical or cylindrical bodies are preferred, as well as disk-shaped pellets or any other suitable geometry such as honeycombs, meshes, hollow bodies, wire arrangements etc.

To form shaped bodies comprising the organometallic framework material several routes exist. Among them (i) molding the organometallic framework material alone or the organometallic framework material in combination with at least one binder and/or at least one other component into a shaped body, for example by pelletizing;

(ii) applying the organometallic framework material onto a (porous) substrate, and (iii) supporting the organometallic framework material material on a porous or nonporous substrate which is then molded into a shaped body; are to be mentioned.

Although not limited with regard to the route to obtain shaped bodies comprising at least one organometallic framework material obtainable by the process according to the present invention, the above-recited routes are preferred within the invention disclosed herein. Presently, zeolites are the most commonly used porous materials which are either molded into shaped bodies or applied onto a (porous) support.

For the step of preparing shaped bodies containing at least one organometallic framework material, all processes of molding a powder and/or crystallites are conceivable. Also, all processes of applying an active component, such as the organometallic framework material, onto a substrate are conceivable. Preparing shaped bodies by a process involving molding is described first, followed by a description of the process of applying said material onto a (porous) substrate.

In the context of the present invention, the term "molding" refers to any process by which a substance which does not fulfill the above-mentioned requirement of a shaped body, i.e. any powder, powdery substance, array of crystallites etc., can be formed into a shaped body which is stable under the conditions of its intended use.

While the step of molding at least one organometallic framework material into a shaped body is mandatory, the following steps are optional according to the present invention:

(I) the molding may be preceded by a step of mixing, (II) the molding may be preceded by a step of preparing a paste-like mass or a fluid containing the organometallic framework material, for example by adding solvents, binders or other additional substances, (III) the molding may be followed by a step of finishing, in particular a step of drying.

The mandatory step of molding, shaping or forming may be achieved by any method known to expert to achieve agglomeration of a powder, a suspension or a paste-like mass. Such methods are described, for example, in Ullmann's Enzylopädie der Technischen Chemie, 4$^{th}$ Edition, Vol. 2, p. 313 et seq., 1972, whose respective content is incorporated into the present application by reference.

In general, the following main pathways can be discerned:

(i) briquetting, i.e. mechanical pressing of the powdery material, with or without binders and/or other additives;

(ii) granulating (pelletizing), i.e. compacting of moistened powdery materials by subjecting it to rotating movements; and (iii) sintering, i.e. subjecting the material to be compacted to a thermal treatment.

Specifically, the molding step according to the invention is preferably performed by using at least one method selected from the following group: briquetting by piston presses, briquetting by roller pressing, binderless briquetting, briquetting with binders, pelletizing, compounding, melting, extruding, co-extruding, spinning, deposition, foaming, spray drying, coating, granulating, in particular spray granulating or granulating according to any process known within the processing of plastics or any combination of at least two of the aforementioned methods.

The preferred processes of molding are those in which the molding is affected by extrusion in conventional extruders, for example such that result in extrudates having a diameter of, usually, from about 1 to about 10 mm, in particular from about 1.5 to about 5 mm. Such extrusion apparatus are described, for example, in Ullmann's Enzylopädie der Technischen Chemie, 4th Edition, Vol. 2, p. 295 et seq., 1972. In addition to the use of an extruder, an extrusion press is preferably also used for molding.

The molding can be performed at elevated pressure (ranging from atmospheric pressure to several 100 bar), at elevated temperatures (ranging from room temperature to 300° C.) or in a protective atmosphere (noble gases, nitrogen or mixtures thereof. Any combination of these conditions is possible as well.

The step of molding can be performed in the presence of binders and/or other additional substances that stabilize the materials to be agglomerated. As to the at least one optional binder, any material known to expert to promote adhesion between the particles to be molded together can be employed. A binder, an organic viscosity-enhancing compound and/or a liquid for converting the material into a paste can be added to the organometallic framework material, with the mixture being subsequently compacted in a mixing or kneading apparatus or an extruder. The resulting plastic material can then be molded, in particular using an extrusion press or an extruder, and the resulting moldings can then be subjected to the optional step of finishing, for example drying and/or calcining.

A number of inorganic compounds can be used as binders. For example, according to U.S. Pat. No. 5,430,000, titanium dioxide or hydrated titanium dioxide is used as the binder. Examples of further prior art binders are:

hydrated alumina or other aluminum-containing binders (WO 94/29408);

mixtures of silicon and aluminum compounds (WO 94/13584);

silicon compounds (EP-A 0 592 050);

clay minerals (JP-A 03 037 156);

alkoxysilanes (EP-B 0 102 544);

amphiphilic substances;

graphite.

Other conceivable binders are in principle all compounds used to date for the purpose of achieving adhesion in powdery materials. Compounds, in particular oxides, of silicon, of aluminum, of boron, of phosphorus, of zirconium and/or of titanium are preferably used. Of particular interest as a binder is silica, where the $SiO_2$ may be introduced into the shaping step as a silica sol or in the form of tetraalkoxysilanes. Oxides of magnesium and of beryllium and clays, for example montmorillonites, kaolins, bentonites, halloysites, dickites, nacrites and anauxites, may furthermore be used as binders. Tetraalkoxysilanes are particularly used as binders in the present invention. Specific examples are tetramethoxysilane, tetraethoxysilane, tetrapropoxysilane and tetrabutoxysilane, the analogous tetraalkoxytitanium and tetraalkoxyzirconium compounds and trimethoxy-, triethoxy-, tripropoxy- and tributoxy-aluminum, tetramethoxysilane and tetraethoxysilane being particularly preferred.

In addition, organic viscosity-enhancing substances and/or hydrophilic polymers, e.g. cellulose or polyacrylates may be used. The organic viscosity-enhancing substance used may likewise be any substance suitable for this purpose. Those preferred are organic, in particular hydrophilic polymers, e.g., cellulose, starch, polyacrylates, polymethacrylates, polyvinyl alcohol, polyvinylpyrrolidone, polyisobutene and polytetrahydrofuran. These substances primarily promote the formation of a plastic material during the kneading, molding and drying step by bridging the primary particles and moreover ensuring the mechanical stability of the molding during the molding and the optional drying process.

There are no restrictions at all with regard to the optional liquid which may be used to create a paste-like substance, either for the optional step of mixing or for the mandatory step of molding. In addition to water, alcohols may be used, provided that they are water-miscible. Accordingly, both monoalcohols of 1 to 4 carbon atoms and water-miscible polyhydric alcohols may be used. In particular, methanol, ethanol, propanol, n-butanol, isobutanol, tertbutanol and mixtures of two or more thereof are used.

Amines or amine-like compounds, for example tetraalkylammonium compounds or aminoalcohols, and carbonate-containing substances, such as calcium carbonate, may be used as further additives. Such further additives are described in EP-A-0 389 041, EP-A-200 260 and WO 95/19222, which are incorporated fully by reference in the context of the present application.

Most, if not all, of the additive substances mentioned above may be removed from the shaped bodies by drying or heating, optionally in a protective atmosphere or under vacuum. In order to keep the organometallic framework material intact, the shaped bodies are preferably not exposed to temperatures exceeding 300° C. However, studies show that heating/drying under the aforementioned mild conditions, in particular drying in vacuo, preferably well below 300° C. is sufficient to at least remove organic compounds from the pores of the organometallic framework material. Generally, the conditions are adapted and chosen depending upon the additive substances used.

The order of addition of the components (optional solvent, binder, additives, material with an organometallic framework material) is not critical. It is possible either to add first the binder, then, for example, the organometallic framework material and, if required, the additive and finally the mixture containing at least one alcohol and/or water or to interchange the order with respect to any of the aforementioned components.

As far as the optional step of mixing is concerned, for example, of the material containing an organometallic framework material and a binder and optionally further process materials (=additional materials), all methods known to the expert in the fields of materials processing and unit operations can be used. If the mixing occurs in the liquid phase, stirring is preferred, if the mass to be mixed is paste-like, kneading and/or extruding are preferred and if the components to be mixed are all in a solid, powdery state, mixing is preferred. The use of atomizers, sprayers, diffusers or nebulizers is conceivable as well if the state of the components to be used allows the use thereof. For paste-like and powder-like materials the use of static mixers, planetary mixers, mixers with rotating containers, pan mixers, pug mills, shearing-disk mixers, centrifugal mixers, sand mills, trough kneaders, internal mixers, internal mixers and continuous kneaders are preferred. It is explicitly included that a process of mixing may be sufficient to achieve the molding, i.e., that the steps of mixing and molding coincide.

The shaped body according to the invention is preferably characterized by at least one of the following properties:

(aa) it extends in at least one direction in space by at least 0.02 mm and that it does not extend in any direction in space by more than 50 mm;
(bb) it is pellet shaped and has a diameter in the range from 1.5 mm to 5 mm and a height in the range from 1 mm to 5 mm;
(cc) it has a resistance to pressure (crush strength) in the range from 2 N to 100 N.

As a second principal pathway for producing shaped bodies containing at least one organometallic framework material, applying said material to a substrate is part of the present invention. Preferably, the substrate is porous. In principle, all techniques for contacting said material with said substrate are conceivable. Specifically, all techniques used for contacting an active material with a porous substrate known from the preparation of catalysts are applicable.

The at least one method of contacting is selected from the group comprising impregnating with a fluid, soaking in a fluid, spraying, depositing from the liquid phase, depositing from gas phase (vapor deposition), precipitating, co-precipitating, dipping-techniques, coating.

As a porous substrate, each shaped body known to the expert can be used, given that the shaped body fulfills the general requirements concerning its geometry as specified in the present application, for example, in items (i) to (iii) above. Specifically, the porous substrate that will be contacted with the organometallic framework material can be selected from alumina, activated alumina, hydrated alumina, silica gels, silicates, diatomite, kaolin, magnesia, activated charcoal, titanium dioxide, and/or zeolites.

While porous substrates are preferred, contacting organometallic framework material with a non-porous body and/or a two-dimensional substrate are conceivable as well. In the case of applying the organometallic framework material onto a non-porous shaped body, shell structures comparable to shell catalysts are obtained. Such configurations, as well as monolithic embodiments, are explicitly included in the present invention, given that they contain at least one organometallic framework material.

Other embodiments customary in catalyst technologies such as application of an active substance in a washcoat and/or structuring the support in honeycombs or in channels or other skeleton-shapes are preferred.

In a further embodiment the organometallic framework material and/or the shaped body formed from the organometallic framework material is contacted with at least one capacity-enhancing agent selected from the group consisting of solvents, complexes, metals, metal hydrides, alanates, alloys, and mixtures of two or more thereof, such as embodiments of the above derived from Pd, Pt, Ni, Ti, and Ru as the metal.

Examples for said capacity-enhancing agent are occluded metal hydrides.

After the formation of the shaped body and before drying and/or before calcination, the shaped body may be washed with at least one suitable washing agent such as at least one compound of the aqueous solvent system used for the reaction mixture. A preferred washing agent is, e.g., water.

According to another aspect, the present invention also relates to the use of the organometallic framework material obtainable by the process of the present invention. Preferably, the organometallic framework material as such or a shaped body containing the organometallic framework material may be employed in application areas in which use is made of the porosity, even more preferably of the high surface area of the organometallic framework material.

Therefore, the present invention also relates to a method of using an organometallic framework material, comprising at least one metal ion and at least one at least bidentate organic compound coordinately bound to said at least one metal ion, said organometallic framework material being obtainable by a process comprising reacting at least one metal salt with at least one at least bidentate compound capable of coordination to the metal ion of said metal salt, in the presence of an aqueous solvent system and at least one base wherein at least one bidentate compound comprises at least carboxy group and at least one further group capable of forming a hydrogen bridge linkage, as catalyst, adsorbent, desiccant, flame retardant, storage material or depot material for active substances, sensor material, pigment, or electronic component.

Preferred application areas are, among others, storage materials, catalysts, and adsorbents. Particularly preferred is the use of the organometallic framework material obtainable by the process of the present invention as material for uptaking and/or storing and/or releasing a gas such as a noble gas, carbon monoxide, carbon dioxide, nitrogen, a hydrocarbon, hydrogen, or a compound generating and/or delivering theses gases, preferably a hydrocarbon gas such as propane, ethane, or methane, or hydrogen, and more preferably methane, under a certain pressure. According to an even more preferred embodiment, the organometallic framework material obtainable by the process of the present invention is used for uptaking and/or storing and/or releasing at least one of these gases wherein the organometallic framework material and/or a shaped body containing the organometallic framework material is present in a container, under a pressure in the range of from 1 to 750 bar inside the container, preferably in the range of from 1 to 150 bar, more preferably in the range of from 1 to 80 bar, still more preferably in the range of 45 to 80 bar and most preferably in the range of from 50 to 80 bar. According to an even more preferred embodiment, said container is comprised in a fuel cell for supplying power to stationary, mobile, and mobile portable applications such as for supplying power to power plants, cars, trucks, busses, cordless tools, cell phones, and laptops. The containers may have cylindrical or non-cylindrical geometry.

According to another preferred embodiment, the present invention relates to a method of catalyzing a reaction of an organic compound wherein the catalyst is an organometallic framework material comprising at least one metal ion and at least one at least bidentate organic compound coordinately bound to said at least one metal ion, obtainable by a process comprising reacting at least one metal salt with at least one at least bidentate compound capable of coordination to the metal ion of said metal salt, in the presence of an aqueous solvent system and at least one base wherein at least one bidentate compound comprises at least carboxy group and at least one further group capable of forming a hydrogen bridge linkage at a pH of the reaction system.

According to an even more preferred embodiment, the present invention relates to a process as described above wherein the reaction of the organic compound is selected from the group consisting of oxidations, reductions, ring opening reactions, C—C coupling reactions, epoxidations, addition reactions, aminations, hydrations, etherifications, alkoxylations, decarbonylations, decarboxylations, dehydrations, dehydrogenations, hydrogenations, isomerizations, C—C bond cleavages, reforming, oligomerizations, polymerizations; catalytic purification of waste gas and wastewater, and photocatalysis.

An especially preferred reaction is the alkoxylation of organic compounds.

The following examples and figures are meant as an illustration of the present invention and are not meant to limit in any way the scope of the present invention.

DESCRIPTION OF THE FIGURES

In FIG. 1, the X axis represents the 2 scale, the Y axis stands for the Lin (Counts).

In FIG. 2, the X axis represents the 2 scale, the y axis stands for the Lin (Counts).

EXAMPLE 1

Figure 1:
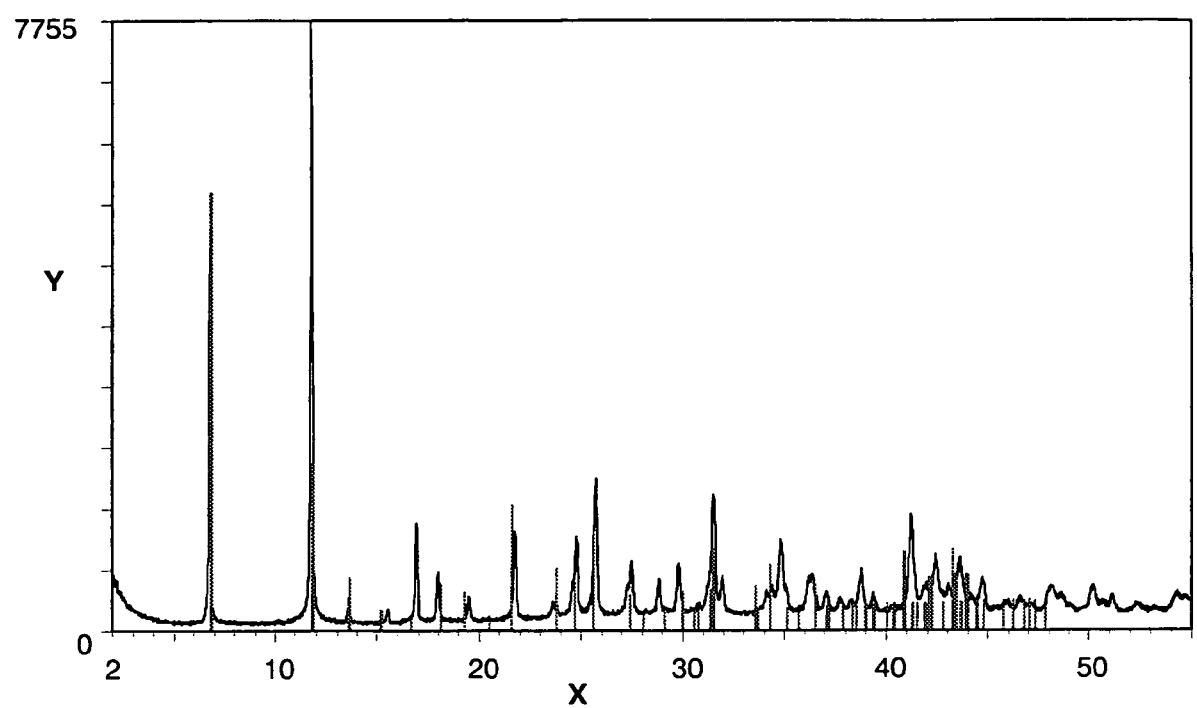
FIG. 1 shows the X-ray diffraction diagram of the organometallic framework material as prepared according to Example 1.

| materials | millimoles | weight calculated/g | weight experimental/g |
|---|---|---|---|
| 2,5-dihydroxy-terephthalic acid (DHTPA) | 20 | 3.96 | 54.0 |
| zinc nitrate tetrahydrate | 40 | 10.46 | 10.5 |
| water | 33.3 | 600.00 | 600.0 |
| sodium hydroxide (1 mole/l) | 78 | 78.00 | 78.0 |
| hydrochloric acid (2 moles/l) | 8 | 4.0 | 4.0 |

In a beaker, 4.0 g DHTPA were dissolved in 400 g bidest. water and 48 g of an aqueous sodium hydroxide solution having a concentration of 1 mole/l at normal pressure and room temperature and at a pH=11. Subsequently, the pH was adjusted to 7.3 with 4 ml of aqueous hydrochloric acid having a concentration of 2 moles/l to give solution 1.

10.5 g of zinc nitrate tetrahydrate were dissolved in 200 g water to give solution 2.

Solution 2 was added dropwise under stirring at normal pressure and room temperature to solution 1 within 1 h. The pH of the solution 2 was kept in a range of from 7.3 to 7.6 by adding, in total, 30 g of aqueous sodium hydroxide solution having a concentration of 1 mole/l.

First, the reaction mixture was clear and yellow. After about 10 min, it became a yellow suspension. Subsequently, the reaction mixture was stirred for about 1 h at normal pressure and room temperature.

The precipitated yellow substance was separated by filtration and washed three times, each time with 10 ml water. Subsequently, the product was dried for 48 h at 60° C. in a circulating air drying oven.

The yield with respect to the amount of zinc employed was 85.8%.

Characterization of the crystal structure was carried out by means of powder X-ray diffraction method at 25° C., a step width of 0.020°, a step time of 3.6 s, and a Cu anode. Determination of the surface was carried out by means of $N_2$ adsorption at 77 K according to DIN 66131 (BET) and/or DIN 66135 (Langmuir).

FIG. 1 shows the X-ray diffraction diagram of the product.

From the adsoprtion isotherm (determined with $N_2$ at 77 K with Micromeritics ASAP 2010) a specific surface area of 230 $m^2/g$ at a relative pressure of $p/p^0=0.4$ was calculated according to the Langmuir model.

In the product, 34 wt.-% of Zn were found by elemental analysis.

The nitrogen content of the dried framework material, determined via elemental analysis, was 0.078 wt.-%.

The prism-shaped crystals had a diameter of from 2 to 10 μm and a length of from 5 to 20 μm, determined via SEM.

EXAMPLE 2

| materials | millimoles | weight calculated/g | weight experimental/g |
|---|---|---|---|
| 2,5-dihydroxy-terephthalic acid (DHTPA) | 20 | 3.96 | 4.0 |
| zinc nitrate tetrahydrate | 60 | 15.68 | 15.7 |
| water | 33.3 | 600.00 | 600.0 |
| sodium hydroxide (1 mole/l) | 88 | 88.00 | 88.0 |
| hydrochloric acid (2 moles/l) | 8 | 4.0 | 4.0 |

In a beaker, 4.0 g DHTPA were dissolved in 400 g bidest. water and 48 g of an aqueous sodium hydroxide solution having a concentration of 1 mole/l at normal pressure and room temperature and at a pH=11. Subsequently, the pH was adjusted to 7.3 with 4 ml of aqueous hydrochloric acid having a concentration of 2 moles/l to give solution 1.

10.5 g of zinc nitrate tetrahydrate were dissolved in 200 g water to give solution 2.

Solution 2 was added dropwise under stirring at normal pressure and room temperature to solution 1 within 1 h. The pH of the solution 2 was kept in a range of from 7.3 to 7.6 by adding, in total, 40 g of aqueous sodium hydroxide solution having a concentration of 1 mole/l.

First, the reaction mixture was clear and yellow. After about 10 min, it became a yellow suspension. Subsequently, the reaction mixture was stirred for about 1 h at normal pressure and room temperature.

The precipitated yellow substance was separated by filtration and washed three times, each time with 10 ml water. Subsequently, the product was dried for 48 h at 60° C. in a circulating air drying oven.

The yield with respect to the amount of zinc employed was 65.0%.

Characterization of the crystal structure was carried out by means of powder X-ray diffraction method at 25° C., a step width of 0.020°, a step time of 3.6 s, and a Cu anode. Determination of the surface was carried out by means of $N_2$ adsorption at 77 K according to DIN 66131 (BET) and/or DIN 66134 (Langmuir)

Figure 2:
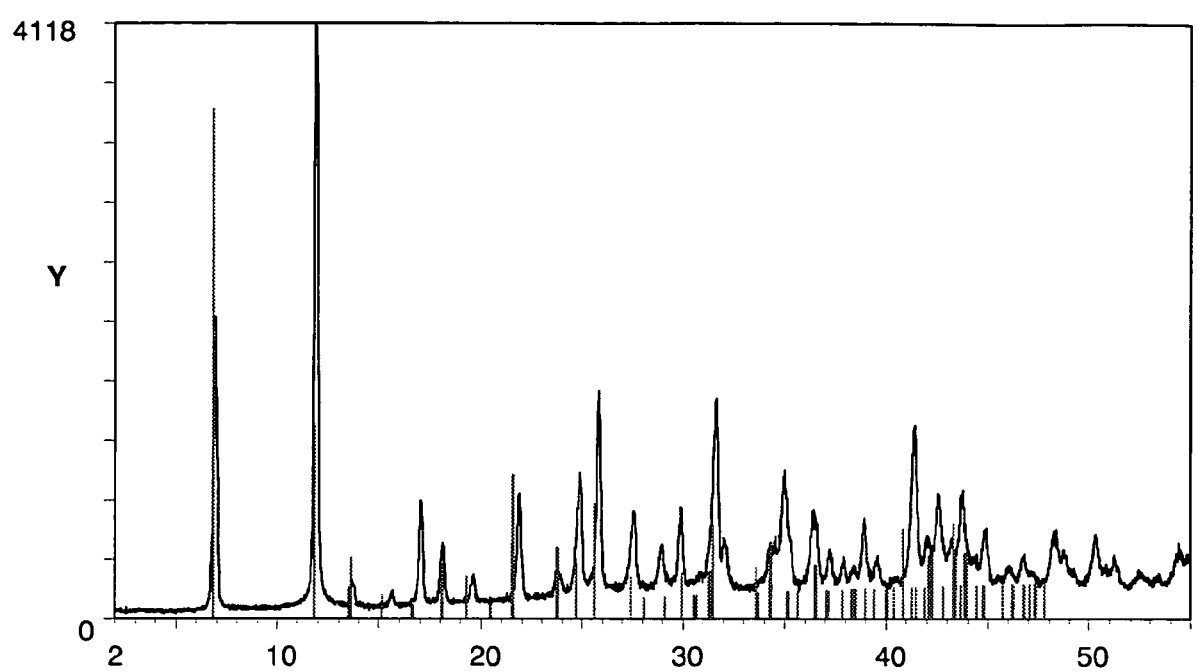
FIG. 2 shows the X-ray diffraction diagram of the organometallic framework material as prepared according to Example 2.

FIG. 2 shows the X-ray diffraction diagram of the product.

From the adsoprtion isotherm (determined with $N_2$ at 77 K with Micromeritics ASAP 2010) a specific surface area of 240 $m^2/g$ at a relative pressure of $p/p^0=0.4$ was calculated according to the Langmuir model.

In the product, 34 wt.-% of Zn were found by elemental analysis.

The nitrogen content of the dried framework material, determined via elemental analysis, was 0.078 wt.-%.

The prism-shaped crystals had a diameter of from 2 to 10 µm and a length of from 5 to 20 µm, determined via SEM.

We claim:

1. A process for preparing an organometallic framework material comprising reacting at least one metal salt with at least one at least bidentate compound capable of coordinating to the metal ion of said metal salt, in the presence of an aqueous solvent system and at least one base wherein at least one bidentate compound comprises at least two carboxy groups and at least one hydroxy group which is capable of forming a hydrogen bridge linkage.

2. A process as claimed in claim 1 wherein the at least one at least bidentate compound comprises two carboxy groups.

3. A process as claimed in claim 1 wherein the at least one at least bidentate compound comprises two hydroxy groups.

4. A process as claimed in claim 1 wherein the at least one bidentate compound is dihydroxy terephthalic acid.

5. A process as claimed in claim 1 wherein the aqueous solvent system comprises water and at least one compound comprising at least one hydroxy group.

6. A process as claimed in claim 1 wherein the aqueous solvent system comprises at least one alcohol selected from the group consisting of methanol, ethanol, n-propanol, and isopropanol.

7. A process as claimed in claim 1 wherein the at least one base is an alkali metal hydroxide, an alkaline earth metal hydroxide and/or a basic metal hydroxide which is at least partially soluble or miscible in the aqueous solvent system.

8. A process as claimed in claim 1 wherein the at least one base is sodium hydroxide or potassium hydroxide or a mixture of sodium hydroxide and potassium hydroxide.

9. A process as claimed in claim 1 wherein the reaction of the at least one metal salt with the at least one bidentate compound is carried out at a pH in the range of from 3 to 9.

10. A process as claimed in claim 1 wherein the reaction of the at least one metal salt with the at least one bidentate compound is carried out at a pH in the range of from 7.3 to 7.6.

11. A process as claimed in claim 1 wherein the at least one metal salt is a salt of Zn, Cu, Co, Ni, Pd, Pt, Ru, Rh, Fe and mixtures of two or more thereof.

12. A process as claimed in claim 1 wherein the metal salt is a salt of Zn, Co, Cu and/or Fe.

13. A process for preparing an organometallic framework material comprising reacting at least one metal salt with at least one at least bidentate compound capable of co-ordination to the metal ion of said metal salt, in the presence of an aqueous solvent and at least one alkali metal hydroxide or alkaline earth metal hydroxide wherein the at least one bidentate compound comprises two hydroxy groups and two carboxy groups.

14. A process as claimed in claim 13 wherein the at least one bidentate compound is dihydroxy terephthalic acid.

15. A process as claimed in claim 13 wherein the at least one hydroxide is sodium hydroxide.

16. A process as claimed in claim 13 wherein the at least one metal salt is a zinc salt.

17. A process as claimed in claim 13 wherein the aqueous solvent is water.

18. A process as claimed in claim 13 wherein the reaction of the at least one metal salt with the at least one bidentate compound is carried out at a pH in the range of from 3 to 9.

19. A process for preparing an organometallic framework material comprising reacting a zinc salt with a bidentate compound in the presence of an aqueous solvent and sodium hydroxide wherein the bidentate compound is dihydroxy terephthalic acid.

20. A process as claimed in claim 18 wherein the aqueous solvent is water.

21. A process as claimed in claim 1 wherein the reaction of the at least one metal salt with the at least one bidentate compound is carried out at a pH in the range of from 7.0 to 8.0.

22. A process for preparing an organometallic framework material comprising reacting a zinc salt with dihydroxy terephthalic acid in the presence of water as solvent and sodium hydroxide wherein the reaction is carried out at a pH in the range of from 7.3 to 7.6.

23. A method of using an organometallic framework material, comprising at least one metal ion and at least one at least bidentate organic compound coordinately bound to said at least one metal ion, said organometallic framework material being obtainable by a process comprising reacting at least one metal salt with at least one at least bidentate compound capable of coordination to the metal ion of said metal salt, in the presence of an aqueous solvent system and at least one base wherein at least one bidentate compound comprises at least carboxy group and at least one hydroxy group comprising the step of catalyzing, adsorbing, desiccating, flame retarding, storing or depositing active substances, sensor material, pigment, or electronic component.

24. A method of catalyzing a reaction of an organic compound comprising the step of reacting an organic compound catalyzed by a catalyst wherein the catalyst is an organometallic framework material comprising at least one metal ion and at least one at least bidentate organic compound coordinately bound to said at least one metal ion, obtainable by a process comprising reacting at least one metal salt with at least one at least bidentate compound capable of coordination to the metal ion of said metal salt, in the presence of an aqueous solvent system and at least one base wherein at least one bidentate compound comprises at least carboxy group and at least one hydroxy group.

25. A method as claimed in claim 24 wherein the reacting of the organic compound is selected from the group consisting of oxidizing, reducing, ring opening, C—C coupling, epoxidizing, adding, aminating, hydrating, etherificating, alkoxylating, decarbonylating, decarboxylating, dehydrating, dehydrogenating, hydrogenating, isomerizing, C—C bond cleaving, reforming, oligomerizing, polymerizing, catalytic purifying of waste gas and wastewater, and photocatalysing.

* * * * *